United States Patent [19]

Miyasaka et al.

[11] Patent Number: 4,700,224
[45] Date of Patent: Oct. 13, 1987

[54] METHOD OF IMAGE PROCESSING FOR THE MEASUREMENT OF TOOL WEAR

[75] Inventors: Kaneyoshi Miyasaka, Toride; Nobushige Sawai; Ryoji Murata, both of Ibaraki, all of Japan

[73] Assignees: Agency of Industrial Science & Technology; Ministry of International Trade & Industry, both of Tokyo, Japan

[21] Appl. No.: 845,339

[22] Filed: Mar. 28, 1986

[30] Foreign Application Priority Data

Jun. 20, 1985 [JP] Japan .................................. 60-134988

[51] Int. Cl.$^4$ ............................................. H04N 7/18
[52] U.S. Cl. ..................................... 358/101; 358/106; 358/107; 364/521; 382/8
[58] Field of Search ....................... 358/101, 106, 107; 382/8; 364/518, 521, 552, 474

[56] References Cited

U.S. PATENT DOCUMENTS

| | | | |
|---|---|---|---|
| 4,380,025 | 4/1983 | Deane | 358/106 |
| 4,484,081 | 11/1984 | Cornyn, Jr. et al. | 358/106 |
| 4,491,962 | 1/1985 | Sakou et al. | 382/8 |
| 4,570,181 | 2/1986 | Yamamura | 358/107 |
| 4,598,384 | 7/1986 | Shaw et al. | 364/521 |

Primary Examiner—Howard W. Britton
Assistant Examiner—John K. Peng
Attorney, Agent, or Firm—Oblon, Fisher, Spivak, McClelland & Maier

[57] ABSTRACT

An image processing system adapted to measure tool wear by imaging the worn portion of a tool with an ITV to produce images thereof together with surrounding portions, comparing the brightness distributions of the images with each other, and carrying out image processing by use of a brightness threshold value set at a boundary between a region wherein variation of the brightness distribution occurs and a region wherein it does not occur.

3 Claims, 10 Drawing Figures

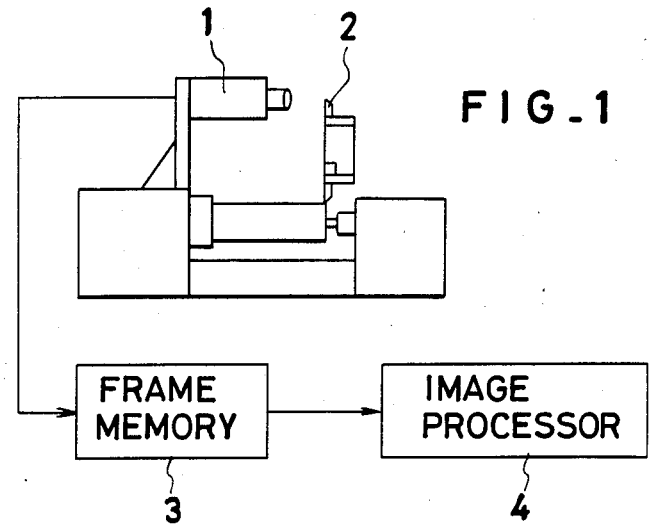
FIG_1
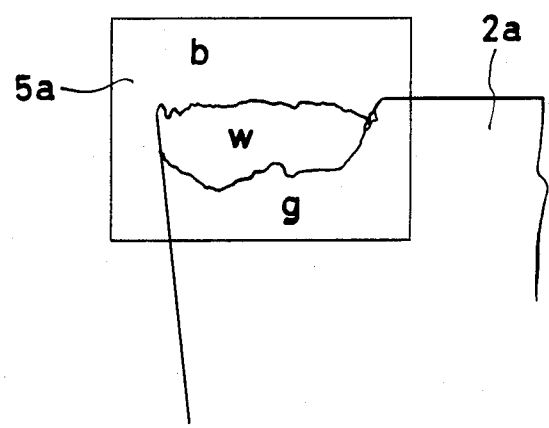
FIG_2

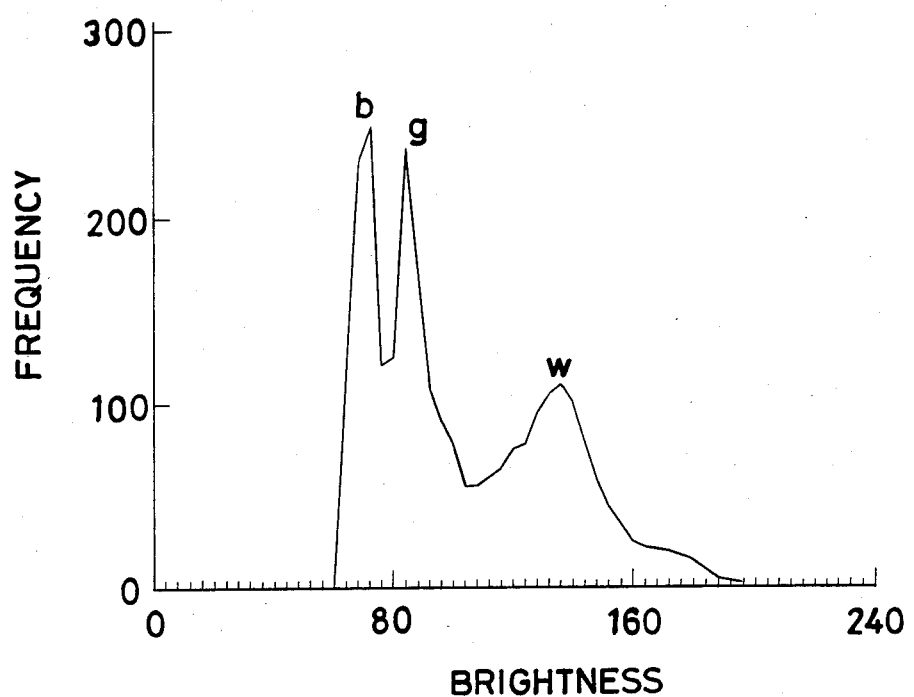

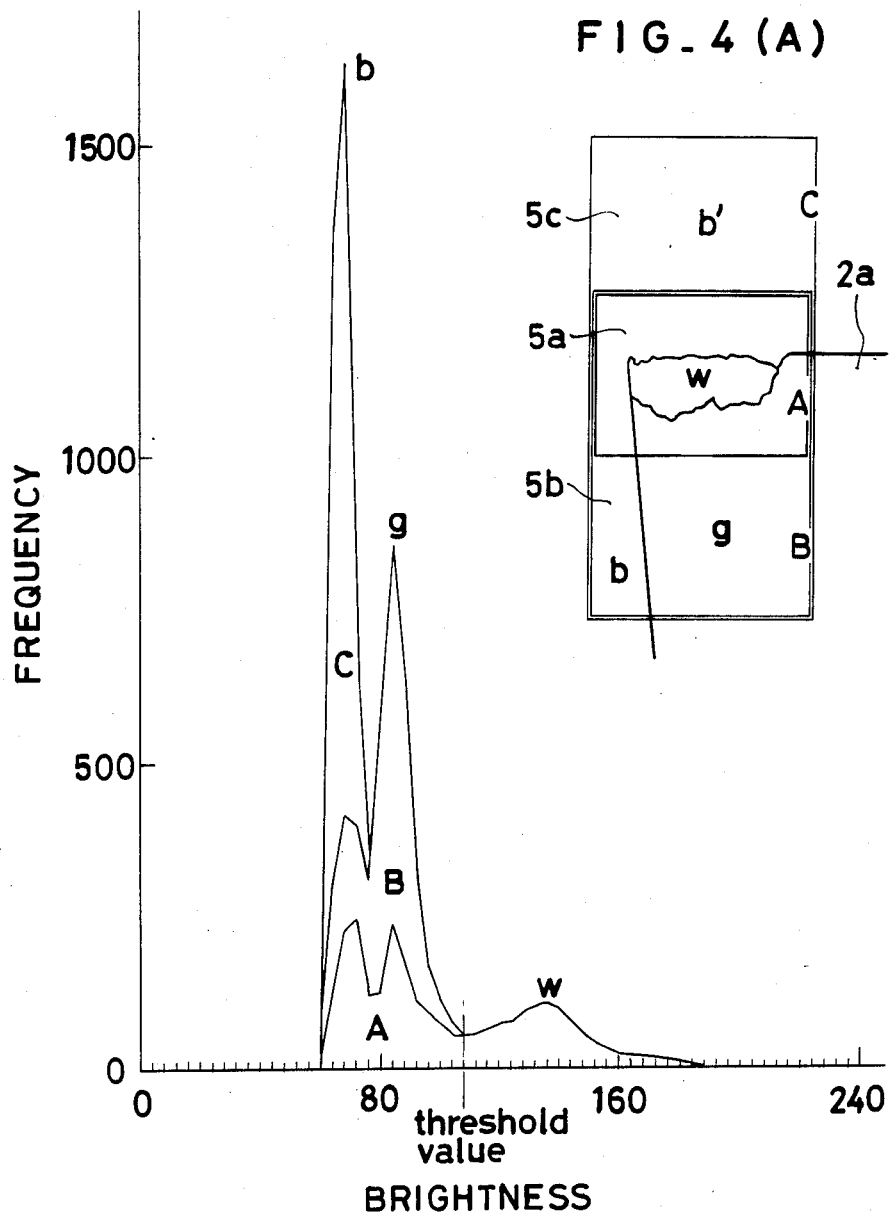

METHOD OF IMAGE PROCESSING FOR THE MEASUREMENT OF TOOL WEAR

FIELD OF THE INVENTION AND RELATED ART STATEMENT

This invention relates to an image processing system for use in measurement of tool wear employing an industrial television (ITV) camera, and more particularly to a method for determining the brightness threshold value for digitizing an image of the worn portion of a tool in the binary system.

In the measurement of tool wear, the general practice is to examine the tool after it has been used for cutting for a prescribed period of time in order to determine the wear width and the like. Through their research into methods for determining the tool wear profile by processing images of the tool obtained by use of an ITV camera, the inventors have learned that it is first necessary to divide the image obtained from the ITV camera into the tool wear portion and other portions, i.e. to digitize the image information in the binary system. For such digitization it is necessary to set a brightness threshold value. Up to now this has been done through a process of trial and error. For automating the aforesaid wear measurement operation, therefore, there is required a system whereby the brightness thereshold value employed in digitizing the image information can constantly be maintained at an appropriate value matched to the tool imaging conditions and changes in the illumination conditions etc.

OBJECT AND SUMMARY OF THE INVENTION

An object of the invention is to provide a system which enables ready determination of an appropriate brightness threshold value for use when the worn portion of a tool is to be displayed as a visible image.

The present invention accomplishes this object by providing an image processing system comprising means to take the image of an ITV camera of the worn portion of a tool together with surrounding portions, defining a window framing a region of said image corresponding to the worn portion and portions other than the worn portion, measuring the brightness distribution within the region framed by the window, comparing said brightness distribution with the brightness distribution within a region framed by a window expanded to frame the region framed by said window together with additional portions other than the worn portion, setting a brightness threshold value at a value falling between a region wherein variation of the brightness distribution occurs and a region in which it does not occur, and digitizing image information in the binary system using the so-obtained threshold value.

In the present invention, therefore, since the brightness distribution is measured for a plurality of images including the worn portion of the tool together with different surrounding portions and the brightness threshold value is set at a value falling between regions wherein brightness distribution does not occur, it become possible to set an appropriate brightness threshold value at all times.

The other objects and features of the invention will better understood from the following explanation made with reference to the drawings.

BRIEF EXPLANATION OF THE DRAWINGS

FIG. 1 is an explanatory view of an embodiment of the image processing system according to the present invention.

FIG. 2 is an explanatory view showing how a window is defined with respect to the image of a worn portion of a tool.

FIG. 3 is a graph showing the brightness distribution within the window of FIG. 2.

FIG. 4(A) is an explanatory view showing a case in which a plurality of windows are defined.

FIG. 4(B) is a graph showing the state of brightness distribution within the respective windows of FIG. 4(A).

DESCRIPTION OF THE PREFERRED EMBODIMENT

Figure 5:
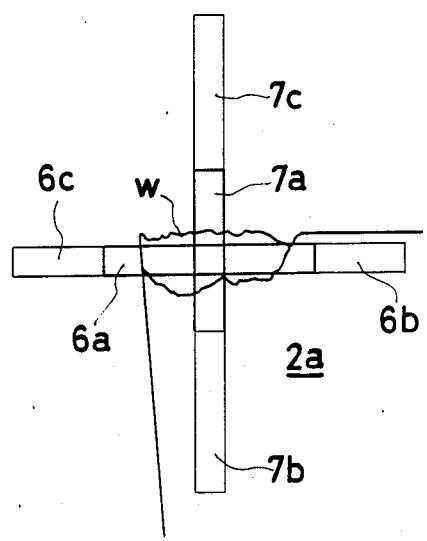
FIG. 5 is an explanatory view showing another manner of defining windows with respect to the image of a worn portion of a tool.

FIG. 1 shows an embodiment of the system according to the present invention comprising an ITV camera used for imaging the worn portion of a tool 2 along with surrounding portions, and a video frame memory 3 in which the image produced by the ITV camera 1 is stored. As the memory 3 there can be used, for example a 512×512 bit (X direction of the image×Y direction) 256-brightness-gradation, three-dimensional digital memory.

In illuminating the tool for imaging, it is preferable to appropriately utilize an angle of relief of the tool so as to illuminate the worn portion more brightly than the other portions. This is not an absolute requirement, however, and the opposite mode of illumination can also be used.

The memory 3 is connected with an image processor 4 for processing the image stored in the memory 3. As shown in FIG. 2, in the image processor 4 there is first defined a window 5a on the order of, for example, 60×44 bits which frames a region of the image including a worn portion w near the cutting edge of the tool 2a, a non-worn portion g of the tool 2a, and a background portion b of the tool 2a. The brightness distribution within the region framed by the window 5a is then measured and stored. An example of the brightness distribution obtained by this process is shown in FIG. 3. In this figure, the brightness distribution is represented on the x-axis in units of 4 brightness gradations. As will be understood from this example, the brightness distribution clearly exhibits one peak for the worn portion w in the vicinity of 136, another peak for the non-worn portion g in the vicinity of 84 and another peak for the background portion b in the vicinity of 72.

Next, as shown in FIG. 4(A), the image processor 4 defines an expanded window 5b framing a region "B" which includes the region "A" of the aforesaid window 5a and is further extended to include a non-worn portion g of the tool 2a and a background portion b of the tool 2a. The brightness distribution within the region "B" framed by the expanded window 5b is then measured and stored. Thereafter, if necessary, the window is expanded into a window 5c further including a region "C" including a background portion b' (i.e. to include "5a"+"5b"+"5c") and the brightness distribution within the region framed by the window 5c is measured and stored.

An example of the results obtained by measuring the brightness distribution within windows defining different regions in this way is shown in FIG. 4(B). In FIG. 4(B), the curve "A" represents the brightness distribution within the region "A" and is the same as the curve of FIG. 3. The curve "B" represents the brightness distribution within the two regions "B", and the curve "C" represents the brightness distribution within the three regions "C". As will be understood from FIG. 4(B), the brightness distribution corresponding to the worn portion w of the tool 2a remains substantially the same irrespective of change in the size of the defined window, whereas the brightness distributions corresponding to the non-worn portion g and the background portion b vary greatly depending on the size of the defined window. Therefore, if the brightness distributions stored for the respective windows are compared in the image processor 4 by means of a comparator and the brightness threshold value is set at a brightness value falling between the region in which the brightness distribution varies and the region in which the brightness distribution does not vary, it then becomes possible to properly digitize the image information. If, as was mentioned as being preferable above, the worn portion is illuminated more brightly than the other portions, the minimum brightness in the region in which the brightness distribution does not change (in the foregoing example, the brightness of 108 in FIG. 4(B) is set as the brightness threshold value.

Although in the foregoing embodiment a comparison was carried out among the windows 5a, 5b and 5c, the brightness threshold value can also be obtained from a comparison of the brightness distribution of the window 5b with that of the window 5a.

Moreover, it is not necessary to define the window to include the whole of the worn portion w. Alternatively, as shown in FIG. 5, it is possible to first define a narrow window 6a (or 7a) including one part of the worn portion w which is expanded to include the regions 6b, 6c (7b, 7c) on opposite sides thereof, and then to set the brightness threshold value on the basis of a comparison of the brightness distributions within these regions.

Once the brightness threshold value has been set in this manner, the worn portion can be defined and displayed from a binary image obtained by comparing the threshold value and the brightness of the image. In this case, however, the following problem may arise. Although the logic level within the profile of the worn portion determined by digitizing the image should of course be either 1 or 0 throughout, in actual measurement there are sometimes found dark spots within the profile where the logic level is inverted. That is to say, there may be spots within the worn portion which have a brightness that is lower than the threshold value. As a result, conventional image processing techniques have been incapable of precisely determining the region of tool wear. The present invention overcomes this problem as will be described below and makes it possible to display the profile of the worn portion unhindered by the existence of dark spots.

Figure 6:
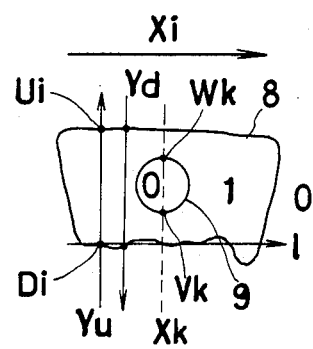
FIG. 6 is an explanatory view regarding the image processing in the case where the worn portion of the tool includes a dark spot.

First assume that the digitized image obtained in the manner described in the foregoing includes no dark spots. In this case, if the value of the bits along a line lying in the x direction such as the line 1 in FIG. 6 should be examined in succession, there may be found a number of change-over points at which the logic level changes from 1 to 0 or vice versa. On the other hand, when the same examination is made along a line lying in the y direction, there will, in view of the nature of tool wear, be found only one change-over point where the logic level changes from 1 to 0 and one change-over point where it changes from 0 to 1. Therefore, by using this characteristic of tool wear, it is possible to determine the wear boundary by checking each bit in the y direction to determine whether it is 0 or 1. On the other hand, however, when there is a dark spot 9 within the worn portion profile 8 as shown in FIG. 6 (the logic level within the profile 8 being 1 and that outside the profile and within any dark spots being 0), then as indicated by the arrows Yu and Yd, there will in each of the upward and downward directions be extracted one 0 to 1 change-over point followed by a 1 to 0 change-over point, and if the upper change-over point for the Xi-th line (i=1, 2 . . . , n) is defined as Ui, the lower change-over point as Di, the upper change-over point of the dark spot 9 as Wk and the lower change-over point of the dark spot 9 as Vk, the result of the measurement will be as shown in the following Table.

TABLE

| | Yu | Yd |
|---|---|---|
| $X_1$ | $U_1 D_1$ | $U_1 D_1$ |
| $X_2$ | $U_2 D_2$ | $U_2 D_2$ |
| $X_3$ | $U_3 D_3$ | $U_3 D_3$ |
| . | . . | . . |
| . | . . | . . |
| $X_i$ | $U_i D_i$ | $U_i D_i$ |
| . | . . | . . |
| . | . . | . . |
| $X_K$ | $V_K D_K$ | $U_K W_K$ |
| . | . . | . . |
| . | . . | . . |
| $X_n$ | $U_n D_n$ | $U_n D_n$ |

Figure 7A:
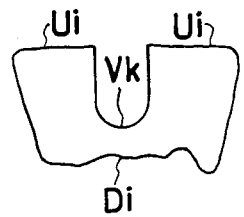
FIG. 7(A) is an explanatory view regarding image processing wherein the worn portion having the dark spot of FIG. 6 is displayed on the basis of change-over points extracted in the upward direction.
Figure 7B:
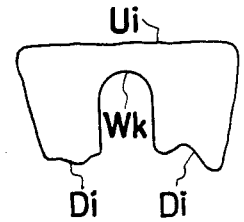
FIG. 7(B) is an explanatory view regarding image processing wherein the worn portion having the dark spot of FIG. 6 is displayed on the basis of change-over points extracted in the downward direction.
Figure 7C:
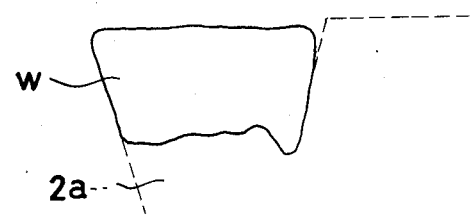
FIG. 7(C) is an explanatory view showing the worn portion of the tool as imaged after the removal of the dark spot shown in FIGS. 7(A) and 7(B).

The change-over points in the upward and downward directions are separately represented, the shape when the extraction is carried out in the direction of the arrow Yu will, as can be seen in FIG. 7(A), show the dark spot to be continuous with the upper line, while the shape when the extraction is carried out in the direction of the arrow Yd will, as can be seen in FIG. 7(B), show the dark spot to be continuous with the lower line. The shapes shown in FIGS. 7(A) and 7(B) have obviously been affected by a dark spot and do not show the true region of wear. However, even with regard to a region that has a dark spot, if, with respect to the Xk-th line, there is used the lower change-over point Dk when extraction is carried out in the upward direction and the upper change-over point Uk when the extraction is carried out in the downward direction, the form obtained will, as shown in FIG. 7(C), represent the profile of the worn portion with the dark spot removed.

Thus it is possible to extract a profile of the worn portion free from the effect of dark spots by a very simple method.

Experiments carried out by the inventors have confirmed that the profile of the worn surface extracted by the method of this invention very closely approximates that of the actual wear portion.

Although the foregoing description relates mainly to the imaging of wear on the tool flank, the present invention is of course not limited to the imaging of flank wear.

As is clear from the foregoing, the image processing system according to this invention makes it possible to determine an appropriate brightness threshold value for digitation processing of the worn portion image and to obtain an accurate image of the tool wear profile by a simple method using a simple device, in a manner that is readily adaptable to changes in the tool wear portion imaging conditions, the tool illumination conditions and the like.

What is claimed is:

1. A method image processing for the measurement of tool wear comprising the steps of:

producing an image of a worn portion of a tool together with surrounding portions by means of television camera;

defining a window framing a region of said image corresponding to the worn portion and portions other than the worn portion;

measuring the brightness distribution within the region framed by the window, comparing said brightness distribution with the brightness distribution within a region framed by a window expanded to frame the region framed by said window together with additional portions other than the worn portion, setting a brightness threshold value at a brightness value falling between a region wherein variation of the brightness distribution occurs and a region in which it does not occur; and digitizing image formation in the binary system using the so-obtained theshold value and displaying an image of the worn portion.

2. A method for measurement of tool wear according to claim 1 wherein the portions other than the worn portion are an unworn portion and a background portion of the tool.

3. A method for measurement of tool wear according to claim 1 wherein an image of the wear portion is displayed by using the brightness threshold value to bidirectionally scan the image information from top to bottom and from bottom to top.

* * * * *